(12) United States Patent
Vachon et al.

(10) Patent No.: US 6,306,419 B1
(45) Date of Patent: Oct. 23, 2001

(54) MEDICAL USES OF STYRENE SULFONATE POLYMERS

(75) Inventors: David Vachon, Granada Hills, CA (US); Gary E. Wnek, Midlothian, VA (US)

(73) Assignee: Aegis Biosciences, LLC, Palm Harbor, FL (US)

( * ) Notice: Subject to any disclaimer, the term of this patent is extended or adjusted under 35 U.S.C. 154(b) by 0 days.

(21) Appl. No.: 09/510,864

(22) Filed: Feb. 23, 2000

(51) Int. Cl.[7] .............. A61F 13/00; A61F 2/00; A61K 9/14
(52) U.S. Cl. .......... 424/422; 424/423; 424/443; 424/449; 424/486
(58) Field of Search .................. 424/443, 422, 424/423, 486, 449; 604/256

(56) References Cited

U.S. PATENT DOCUMENTS

| | | | |
|---|---|---|---|
| 3,925,280 | 12/1975 | Lundberg et al. | 260/23 R |
| 5,296,235 | 3/1994 | Sawayanagi et al. | 424/486 |
| 5,389,092 * | 2/1995 | Guillemet et al. | 604/304 |
| 5,407,715 | 4/1995 | Buddenhagen et al. | 428/35.7 |
| 5,429,589 | 7/1995 | Cartmell et al. | 602/42 |
| 5,468,574 | 11/1995 | Ehrenberg et al. | 429/33 |
| 5,498,248 * | 3/1996 | Milder | 604/265 |
| 5,725,817 | 3/1998 | Milder | 264/104 |
| 5,753,251 | 5/1998 | Burrell et al. | 424/426 |
| 5,759,564 | 6/1998 | Milder et al. | 424/426 |
| 5,770,255 | 6/1998 | Burrell et al. | 427/2.1 |
| 5,837,275 | 11/1998 | Burrell et al. | 424/409 |
| 5,840,387 * | 11/1998 | Berlowitz-Tarrant et al. | 428/36.91 |
| 5,853,745 * | 12/1998 | Darouiche | 424/423 |
| 5,985,990 * | 11/1999 | Kantner et al. | 524/765 |

FOREIGN PATENT DOCUMENTS

| | | | |
|---|---|---|---|
| 2339733 | 11/1990 | (JP) | A61K/31/795 |
| 2339734 | 11/1990 | (JP) | A61L/33/00 |
| 5001674 | 8/1993 | (JP) | H01M/4/86 |
| 7149688 | 5/1995 | (JP) | G01N/33/48 |

* cited by examiner

*Primary Examiner*—Thurman K. Page
*Assistant Examiner*—Isis Ghali
(74) *Attorney, Agent, or Firm*—Heslin, Rothenberg, Farley & Mesiti P.C.

(57) ABSTRACT

Wound dressings and coated implantable medical devices include a styrene sulfonate polymer. Organic and inorganic therapeutic agents may be incorporated in the copolymer. Inorganic therapeutic agents are oligodynamic metals, especially silver.

33 Claims, 1 Drawing Sheet

MEDICAL USES OF STYRENE SULFONATE POLYMERS

FIELD OF THE INVENTION

The invention relates to styrene sulfonate polymers and their use in moist wound dressings and coatings for implantable medical devices.

BACKGROUND OF THE INVENTION

Research has established that healing of wounds such as burns, skin ulcers, pressure sores and traumatic injuries is facilitated when the wound bed is kept moist and clean. Moist wound dressings are particularly useful for this purpose and have become an accepted therapy for treating wounds. In this context, moist means that the dressing keeps the wound moist, and not necessarily that the dressing is moist when applied to the wound. It is postulated that these dressings promote optimum physiological conditions for healing in the wound by maintaining or promoting tissue hydration. When applied to dry wounds, the dressings rehydrate dessicated tissue, either by preventing loss of water vapor from the site or by directly transferring moisture to the tissue. When applied to exudating wounds, the dressings absorb the exudate and promote hydration of tissue. Autolytic debridement of necrotic tissue and/or formation of new tissue occurs more readily under these conditions. In addition, a variety of growth factors that promote wound healing are present in the exudates from the wounds (see Howell, J. M., Current and Future Trends in Wound Healing, Emerg. Med. Clin. North Amer., 10, 655–663 (1992)), and it is believed that moist wound dressings that can absorb fluids from the exudate promote healing by minimizing loss of these growth factors from the wound bed.

Several types of moist wound dressings are commercially available, including hydrogels, hydrocolloids, semipermeable adhesive films, perforated films, alginates, polysacside beads, an d poly urethane foams. These types are distinguished by the physical form of the dressing, by its mechanism of action, and by its chemical composition.

Hydrogel dressings are composed of insoluble polymers having hydrophilic sites that interact with aqueous solutions, and can absorb and retain a significant volume of fluid. Use of these dressings is growing at a double digit rate, driven by an increasing elderly population afflicted with chronic wounds such as skin ulcers, due to diabetes, or pressure sores, resulting from being bedridden.

Hydrogel dressings have additionally been used as carriers for the delivery of therapeutic agents to a wound site, usually for the treatment of infection. For example, Intrasite gel, an amorphous hydrogel wound treatment manufactured by Smith & Nephew, is approved in the United Kingdom as a carrier for metronidazole for the treatment of fungating and other malodorous wounds. Generally, a medicament or drug used as the therapeutic agent is incorporated in the hydrogel during manufacture of the dressing, or, for film-type dressings, taken up into the polymer by swelling a dry film with an aqueous solution of the therapeutic agent. After the dressing is applied to the wound, the therapeutic agent diffuses into the tissue. It is expected that such therapies that combine treatment of wounds with moist wound dressing with delivery of a drug, especially an antibiotic, would provide a significant benefit to patients. Unfortunately, use of hydrogels as carriers has been severely limited by the composition and resulting physical properties of available products. Many of the commercial moist wound dressings are composed of a crosslinked ethylene oxide polymer. These dressings are typically manufactured by irradiating an aqueous solution of a functionalized polyethylene oxide with ionizing radiation, resulting in a sheet of insoluble gel swollen with water. Any drug to be incorporated prior to the crosslinking step must be stable to this high-energy radiation. Alternately, it is possible to dehydrate the gel following crosslinking and rehydrate with an aqueous solution of the drug. However, dressings composed of polyethylene oxide frequently develop unacceptable cosmetic defects when dehydrated and rehydrated.

"Therapeutic agent," as used herein, includes drugs and medicaments for treatment of pathological conditions and for prophylactic use. Included within the definition are antibacterial agents, anesthetics, cell adhesion peptides, such as RGD peptides, growth factors, spermicides, antiviral agents, antifungal agents, antiparasitic agents, anti-inflammatory agents, antihistamines, analgesics, antineoplastic agents, hormones, kerolytic agents, tranquilizers, vitamins, base-pair nucleotides and cytokines.

In addition, metals having oligodynamic properties are herein defined as therapeutic agents. The antimicrobial effect of certain metals or metal ions at very low concentrations is termed oligodynamic action. Metals having oligodynamic properties include silver, gold, platinum, palladium, mercury, copper, tin, antimony, bismuth, zinc, aluminum and magnesium. Ions are the most active form of these metals. The antibacterial effect of an oligodynamic metal may be increased by electrically injecting the metal ions into solution. This process has been termed oligodynamic iontophoresis. Iontophoretic structures for medical devices have been described in U.S. Pat. No. 5,322,520 and related patents. The patents teach imbedding two dissimilar metals in polymers filled with carbon or other conductive fillers. Ions are forced into the conductive fluid environment using the minute electric currents generated by the galvanic potential difference between the two metals. The dissimilar metals act as electrodes, with a voltage potential therebetween, whereby electrons migrate through the polymer, generating an electric current. Metal ions are driven into the conductive matrix by this very small electric current.

The antimicrobial action of silver ion is particularly well known. For example, silver compounds, such as silver sulfadiazine for treatment of burns, are used routinely in antibacterial salves, and has also been used to coat gauze for burn dressings. Medical devices, such as catheters, coated with a silver-impregnated collagen or polymer are also known. However, there is a need for improved methods of delivering therapeutic agents, including oligodynamic metals, to a site susceptible to infection.

U.S. Pat. No. 5,840,387 to Berlowitz-Tarrant et al. discloses use of a sulfonated copolymer of styrene for delivery of non-silver therapeutic agents. The patent does not disclose a silver-containing polymer or a moist wound dressing comprising a styrene sulfonate polymer.

SUMMARY OF THE INVENTION

It has been surprisingly discovered that styrene sulfonate polymers are useful as moist wound dressings, and particularly, as moist wound dressings that function as carriers for therapeutic agents. The term "styrene sulfonate polymer" as used herein refers to a polymer having residues derived from styrene monomer, the aromatic ring of which is substituted with at least one sulfonate group. The term encompasses homopolymers containing residues derivable from styrene sulfonate, and copolymers containing residues derivable from styrene and styrene sulfonate, as well as copolymers containing residues of other comonomers in addition to styrene and styrene sulfonate. These polymers possess mechanical strength without the need for chemical crosslinking, are soluble in common solvents and can be dehydrated and rehydrated without the formation of cosmetic defects.

In one aspect, the present invention relates to a wound dressing for covering wound that comprises a first layer having a first surface which is contactable with the wound and has disposed thereon a styrene sulfonate polymer comprising structural units of formula I:

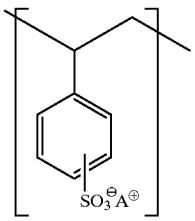

wherein $A^+$ is hydrogen, ammonium, an alkali metal, an oligodynamic metal or the cation of a therapeutic agent. The first layer may be impregnated with or coated with the styrene sulfonate polymer. A second layer of the wound dressing may be a solid film, a perforated film, a woven fabric, a nonwoven fabric, and/or a knit fabric.

In one embodiment, a wound dressing of the present invention additionally comprises a therapeutic agent. Preferred therapeutic agents are oligodynamic metals, and in particular, silver, in the form of silver ion and/or silver metal. Preferred non-silver therapeutic agents are antibacterial agents, anesthetics, growth factors, spermicide, antiviral agents, antifungal agents, antiparasitic agents, antiinflammatory agents, antihistamines, analgesic agents, antineoplastic agents, hormones, kerolytic agents, tranquilizers, vitamins, base-pair nucleotides and/or cytokines.

The styrene sulfonate polymer may include residues derived from at least one olefin comonomer in addition to the residues derived from styrene. The olefin comonomer is preferably ethylene, propylene, butylene, isobutylene, butadiene or isoprene, or a combination of two or more of these. Preferred styrene sulfonate polymers are sulfonated styrene-ethylene-butylene-styrene triblock copolymers, sulfonated reduced statistical styrene butadiene copolymers and sulfonated statistical styrene ethylene copolymers. The term "reduced" is used herein to designated a copolymer that has been hydrogenated in order to reduce residual double bonds, prior to the sulfonation step. The term "statistical" refers to copolymers that are synthesized by methods that are not designed to produce blocks or grafts in the copolymer; these polymers are also commonly referred to as random copolymers.

The styrene sulfonate polymer preferably comprises from 20 to 80% styrene, and preferably has a molecular weight of at least 20,000. At least 15 mole percent of the residues derived from styrene are sulfonated, and preferably at least 35 mole percent of the styrene residues are sulfonated.

In another aspect, the invention relates to a method of treating a wound comprising applying to a wound in need of treatment, a wound dressing, the wound dressing comprising a layer having a first surface contactable with the wound and having a styrene sulfonate polymer disposed thereon.

In yet another aspect, the invention relates to a method of manufacturing a wound dressing comprising applying a styrene sulfonate polymer to a surface of a substrate, wherein the surface is contactable with a wound. A therapeutic agent may also be incorporated in the styrene sulfonate polymer.

In yet another aspect, the invention relates to a coated implantable medical device comprising an implantable medical device having at least one surface and a polymer disposed on a surface of the implantable device, the polymer comprising a styrene sulfonate polymer and at least one of silver ion and silver metal.

In yet another aspect, the invention relates to a composition comprising a styrene sulfonate polymer and at least one of silver ion and silver metal, preferably the silver salt of the styrene sulfonate polymer. The composition may additionally comprise silver metal and/or a non-silver metal. The composition may also additionally comprise a non-silver therapeutic agent. Preferred non-silver therapeutic agents are those listed above. Preferred styrene sulfonate polymers are described above. The composition may be a polymer blend of a sulfonated styrene-ethylene-butylene-styrene triblock copolymer, a sulfonated reduced statistical styrene butadiene copolymer, a sulfonated statistical styrene ethylene copolymer and/or a sulfonated polystyrene In yet another aspect, the present invention relates to a method of controlling infection associated with an implantable medical device comprising coating at least one surface of the implantable medical device with a polymer comprising a silver salt of a styrene sulfonate polymer; and implanting the implantable medical device in a body of a mammal.

In yet another aspect, the present invention relates to a method of manufacturing an implantable medical device, the method comprising coating at least one surface of the implantable medical device with a styrene sulfonate polymer containing at least one of silver ion or silver metal. The styrene sulfonate polymer preferably additionally comprises a therapeutic agent.

DETAILED DESCRIPTION OF THE INVENTION

Figure 1:
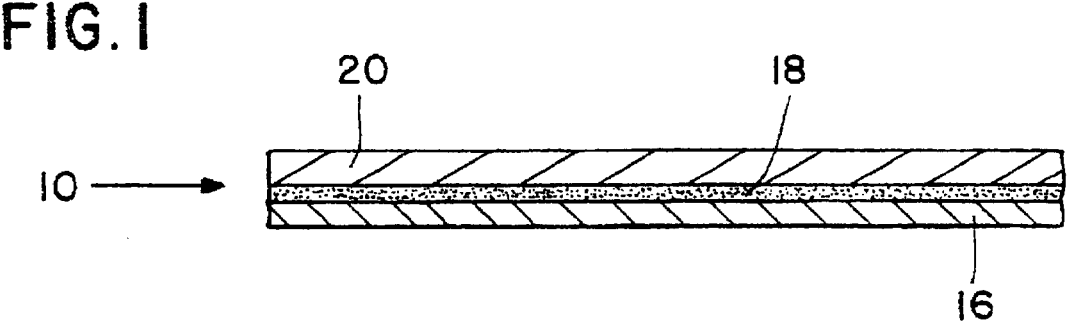
FIG. 1 is a cross sectional view of a wound dressing in the form of a laminate, the laminate being composed of a substrate, an adhesive, and a layer containing a styrene sulfonate polymer.

The styrene sulfonate polymers useful as the wound dressings of the present invention or as the coatings for medical devices of the present invention are hydrophilic, hydrogel-type materials that can absorb and retain a relatively large amount of water or water-containing fluid. In addition, the styrene sulfonate polymers possess good mechanical strength and abrasion resistance when swelled with water, without requiring crosslinking, such that a moist wound dressing containing the styrene sulfonate polymer maintains its integrity without disintegrating. Styrene sulfonate polymers provide a convenient and effective means to deliver therapeutic agents, particularly silver ion, to tissues in contact with the copolymer.

The composition of styrene sulfonate polymers useful for wound dressings or coatings for medical devices typically ranges from about 20% styrene to about 80% styrene. That is, the polymer contains about 20–80% by weight of residues derived from styrene before sulfonation of the aromatic ring of the styrene residues. Homopolymers of styrene may be sulfonated to produce a copolymer containing residues derivable from styrene and styrene sulfonate. The styrene sulfonate polymer may additionally comprise residues derived from at least one olefin comonomer. Preferred olefin comonomers include monoolefins, such as ethylene, propylene, butylene, and isobutylene, and also diolefin monomers, such as butadiene and isoprene. Other comonomers, such as acrylate monomers, may be used, provided that the properties of the copolymer are sufficient for use as a wound dressing. The composition may be adjusted by varying the level of styrene and/or the comonomers(s) to provide desired properties in the end product. Properties that are significant for application as a moist wound dressing are tensile strength, compliance, hydrophilicity (water uptake), and biocompatibility. In order to be useful, the dressing should preferably be strong, elastic, highly conformable, inexpensive, absorbent, and sterilizable. Level of sulfonation largely determines the maximum amount of water taken up by the polymer.

The styrene sulfonate polymer may also be blended with other polymers. These blends, depending on the amount of each polymer and the thermodynamics of mixing, can afford materials ranging from phase-separated to single phase. An advantage of blending is that selected properties of the individual components may be obtained in the resulting material. Block copolymers having both components of the blend in a single chain may be used to the increase the compatibility of the blend components. It should be noted that blending is not limited to polymer pairs, and thus three-component and higher mixtures are possible.

The preferred level of sulfonation of the styrene residues is at least 15 mole percent, and is preferably at least 35 mole percent. However, where a blend of a styrene/styrene sulfonate copolymer with another polymer is utilized, higher levels of styrene sulfonate may be desirable. Sulfonation of the styrene residues is typically performed after completion of the polymerization. Methods for sulfonating styrene copolymers are known in the art. One suitable method is described in U.S. Pat. No. 5,468, 574 to Ehrenberg et al. Therein, sulfur trioxide and triethyl phosphate in a solution of methylene chloride/cyclohexane are used as sulfonating agents for a styrene-ethylene-butylene-styrene block copolymer. Sulfonation of hydrogenated block copolymers of styrene and butadiene to a level of about 25 mole percent is known in the art as described in U.S. Pat. No. 5,239,010 to Balas et al. A preferred method of sulfonating at the aromatic ring of the styrene residues, whereby high levels of sulfonation may be achieved, is described in published PCT application, WO 99/38896. The application discloses the preparation of an acetyl sulfate sulfonation agent by the addition of sulfuric acid to a solution of acetic anhydride in 1,2-dichloroethane (DCE). An appropriate amount of the sulfonation agent is reacted with a styrene copolymer in a DCE solution to yield a copolymer sulfonated to a desired level, up to about 80 mol%.

When an unsulfonated styrene copolymer contains residues derived from a diolefin comonomer, such as butadiene, residual alkene functionality is usually present in the copolymer. In this case, the copolymer may be hydrogenated in order to reduce the double bonds prior to the sulfonation step. The resulting copolymer is referred to as a reduced or hydrogenated copolymer. The copolymer may be hydrogenated by methods known in the art, for example, by hydrogen gas in the presence of catalysts such as Raney Nickel, platinum or palladium. Hydrogenated statistical copolymers of styrene and butadiene are also commercially available.

Several types of styrene-containing polymers are commercially available, including statistical, block and graft copolymers, and combinations of these types. The term "statistical" is well known in the art, and refers to copolymers that are synthesized by methods that are not designed to produce blocks or grafts in the copolymer. (This type of polymer is also commonly referred to as a random copolymer.) The monomers polymerize according to their relative reactivities. Any of these types may be used in manufacturing the wound dressing and coated implantable medical devices of the present invention. Particularly preferred styrene sulfonate polymers are sulfonated styrene-ethylene-butylene-styrene triblock copolymers, statistical sulfonated styrene butadiene copolymers and sulfonated statistical styrene ethylene copolymers.

Unsulfonated styrene-ethylene-butylene-styrene triblock copolymers may be obtained from Shell as the Kraton® series. The styrene content of the Kraton(® copolymers is typically about 30% before sulfonation. Unsulfonated rubbery styrene butadiene copolymers, known as styrene butadiene rubber (SBR) are commercially available from Goodyear. Unsulfonated styrene ethylene copolymers may be obtained from Dow Chemical.

Molecular weight of the polymer preferably ranges from about 20,000 to about 1,000,000, and more preferably from about 50,000 to about 900,000. With regard to a lower limit for molecular weight, highly sulfonated styrene polymers having a relatively low molecular weight may be water soluble. In general, it is desirable that the wound dressings of the present invention contain a styrene sulfonate polymer having a molecular weight sufficiently high that the polymer is not water soluble. Since the preferred level of sulfonation is at least 15% mole percent; molecular weight is preferably at least 20,000. Styrene sulfonate polymers, due to the lack of chemical crosslinks, are typically soluble in common organic solvents. For example, sulfonated SEBS is soluble in tetrahydroflran. Copolymer solutions are advantageously used in manufacturing the wound dressings and coated implantable medical devices of the present invention, and to incorporate therapeutic agents in the same. With regard to an upper limit for molecular weight, in order to control the viscosity of styrene sulfonate polymer solutions during the manufacturing process, it may be desirable to limit the molecular weight of the copolymer to less than about 1,000,000.

Therapeutic agents may be incorporated in a styrene sulfonate polymer for use in the wound dressings and coatings for medical devices of the present invention. These include metals having oligodynamic properties, and in particular, silver, and drugs and medicaments for treatment of pathological conditions and for prophylactic use. Metals having oligodynamic properties include silver, gold, platinum, palladium, mercury, copper, tin, antimony, bismuth, zinc, aluminum and magnesium. A preferred metal is silver, because of its well-known antibacterial properties. The most active form of silver with respect to oligodynamic properties is silver ion. Examples of non-silver therapeutic agents include antibacterial agents, anesthetics, cell adhesion peptides, such as rgd peptides, growth factors, spermicides, antiviral agents, antifungal agents, antiparasitic agents, anti-inflammatory agents, antihistamines, analgesics, antineoplastic agents, hormones, kerolytic agents, tranquilizers, vitamins, base-pair nucleotides and cytokines.

A particular advantage of using styrene sulfonate polymers as a hydrogel-type material in a wound dressing or as a coating for implantable medical devices is that therapeutic agents may be conveniently incorporated in the copolymer. Because styrene sulfonate polymers are soluble in some common organic solvents, a solution of a styrene sulfonate polymer in a suitable organic solvent may be combined with a solution of a therapeutic agent in a compatible solvent. Alternatively, because films of styrene sulfonate polymers may be rehydrated without cosmetic defect, water soluble therapeutic agents may be incorporated in the copolymers by swelling the dehydrated material with an aqueous solution of one or more therapeutic agents.

Silver ion may be incorporated in a styrene sulfonate polymer by preparing the silver salt of the sulfonated styrene residues. This may be conveniently accomplished by combining a solution of a styrene sulfonate polymer with silver nitrate. Alternately, a film of the polymer may be swelled with an aqueous solution of silver nitrate. After preparing a silver salt of a copolymer, finely divided silver metal may be produced in-situ by treating the copolymer with a reducing agent, such as sodium thiosulfate or sodium bisulfite. A wound dressing containing silver in the form of the silver salt of the polymer or of domains of finely divided metal typically has antibacterial properties due to the oligodynamic action of the silver.

Other metals having oligodynamic properties may be incorporated in a styrene sulfonate polymer in a similar way. Generally, a soluble salt of an oligodynamic metal is combined with a solution of the polymer to form a sulfonate salt of the metal, with the sulfonate groups being bound to the polymer backbone. Wound dressings incorporating these metals typically have a similar antibacterial effect. For example, gold, palladium, and iridium may be incorporated in a styrene sulfonate polymer through hydrogen tetrachloroaurate, hydrogen hexachloriridate, and tetraamine palladium (II) chloride, respectively. If desired, the sulfonate salts may be reduced to yield finely divided particles of the metals distributed throughout the polymer.

The antibacterial effect of an oligodynamic metal may be increased using oligodynamic iontophoresis. Two or more dissimilar metals may be incorporated in the styrene sulfonate polymer by combining two or more salts of dissimilar metals with the polymer, either simultaneous or sequentially, and reducing to yield the metal, if desired. One of the metals may also be incorporated in a wound dressing by depositing a film of the metal on a fabric or film substrate before the substrate is coated with the styrene sulfonate polymer solution containing a metal salt of the polymer. For an implantable medical device to be coated with a copolymer composed of a metal salt of a styrene sulfonate polymer, a dissimilar metal may be deposited on the surface of the device before coating. Deposition of the dissimilar metal may be accomplished by physical vapor deposition means, for example, which includes such techniques as sputtering and ion beam deposition. A second metal is then incorporated as the metal salt of the copolymer, and reduced if desired. Iontophoretic effects may theoretically be achieved by incorporating two or more finely divided metal particles in any polymer which is conductive when swollen with water or body fluids, or incorporating finely divided particles of one metal in the polymer, and depositing a second metal on a surface in contact with the polymer. It is expected that many of the hydrophilic polymers suitable as wound dressings would possess antibacterial properties if the metal particles were evenly distributed throughout the polymer. Uniform distribution of metal particles has been difficult to achieve with prior art materials. The styrene sulfonate polymers of the present invention are advantageous in that uniform distributions of very finely divided metal particles are readily prepared. In addition, the styrene sulfonate polymer of the present invention show a surprising stability to reducing agents, being unaffected by the conditions employed to reduce the salt to the metal.

A wound dressing of the present invention, containing a styrene sulfonate polymer, may be fabricated in any convenient form. Preferably, it is fabricated as a substrate having a styrene sulfonate polymer applied thereto or as a laminate having a layer containing a styrene sulfonate polymer. A styrene sulfonate polymer may be applied to a substrate by impregnating, coating and/or encapsulating the same with a styrene sulfonate polymer. Exemplary materials that may be suitable as substrates include porous knitted, woven or nonwoven fabrics. The fabrics may be composed of cotton, wool, rayon, polyamide, polyimide, polypropylene, or polyester fibers. The wound dressing may be secured to the wound by any suitable means, such as tape or wrapping with a fabric strip.

A wound dressing in the form of a laminate is typically composed of a backing, which is optionally coated with an adhesive layer, and a layer containing a styrene sulfonate polymer. The backing may be a solid film, a perforated film, a woven fabric, a nonwoven fabric, a knit fabric, or a laminate of fabrics and/or films. Adhesives suitable for medical use are preferred. The adhesive layer serves to attach the copolymer to the backing, and/or to affix the dressing to the wound or to the skin near the wound. The backing, or the adhesive layer, if an adhesive layer is used, is partially or completely covered with a layer containing the styrene sulfonate polymer. This layer forms the surface which may be placed in contact with the wound during treatment. This layer may be composed of a styrene sulfonate polymer alone, that is, as a film or coating, or of a substrate impregnated, coated and/or encapsulated with the copolymer.

A wound dressing in the form of a laminate is illustrated in FIG. 1. Laminate 10 comprises a backing 16, coated on one surface with an adhesive 18, and a styrene sulfonate polymer-containing layer 20. The laminate may be used to form wound dressings. The dressings may have various configurations including, for example, an island pad configuration or strip dressing configuration. In such configurations, the backing generally extends beyond the styrene sulfonate polymer containing layer in at least two opposing directions. Accordingly, the laminate is sized to be dimensionally smaller in length and/or width than the backing to which it is adhered.

Figure 2:
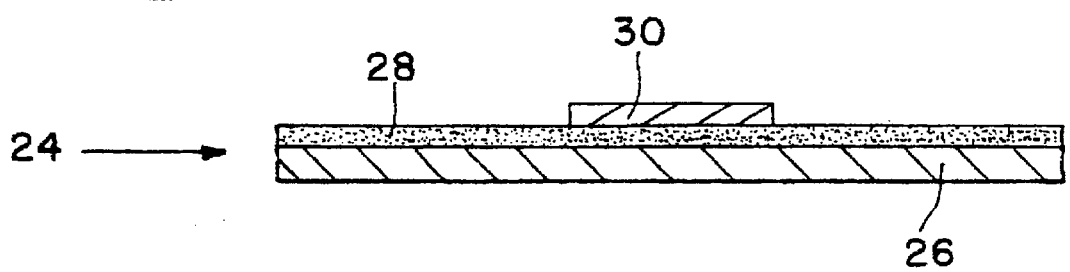
FIG. 2 is a cross sectional view of the dressing illustrated in FIG. 3, taken along line 1—1.
Figure 3:
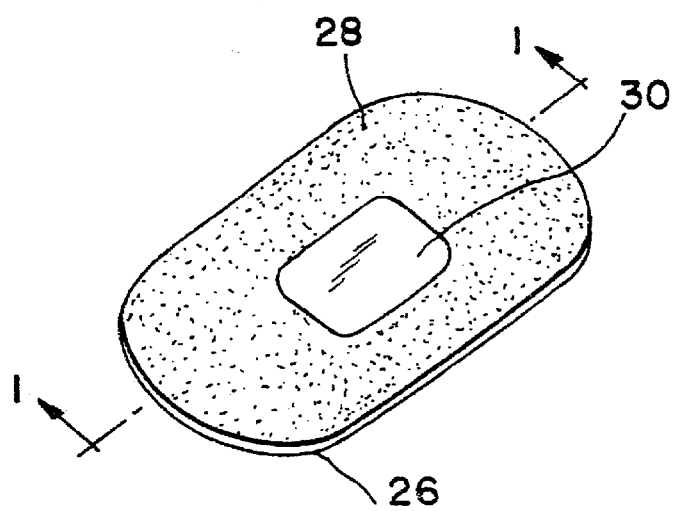
FIG. 3 is a perspective view of a wound dressing in the form of laminate having an island pad configuration.

Referring to FIGS. 2 and 3, an island dressing 24 containing a styrene sulfonate polymer broadly comprises a backing 26, coated on one surface with an adhesive layer 28 and a layer containing a styrene sulfonate polymer 30. In the illustrated dressing configuration, layer 30 is in the form of an island pad, that is, it is not as long as either backing 26 or adhesive layer 28. Portions of adhesive layer 28 are exposed and are used to secure dressing 24 to the body in the same fashion as a conventional adhesive bandage. The exposed adhesive portions may be covered by release papers which may be provided with central tabs to facilitate their removal. The dressing is packaged and sterilized prior to use.

Styrene sulfonate polymers containing a therapeutic agent may be used to coat medical devices for implantation in the body in order to prevent infection. Exemplary therapeutic agents, including silver and non-silver compounds, are listed above. Therapeutic agents, including oligodynamic metals, may be incorporated in a styrene sulfonate polymer as discussed above. Iontophoretic structures may be manufactured by coating the device with a styrene sulfonate polymer containing two or more dissimilar metals. Alternately, the device may be coated with a film containing one of the metals, such as a metal film, or a film of a metal-filled polymer. The device may be coated with a metal film by physical vapor deposition means, for example, sputtering and ion beam deposition. A second metal is then incorporated as the metal salt of a styrene sulfonate polymer, and reduced if desired. Methods for coating with polymers are well known in the art and include such techniques as dipping and spraying. Implantable medical devices that may be coated with a styrene sulfonate polymer containing a therapeutic agent in order to prevent infection after implantation are ones that come into contact with a body fluid or tissue for a period of time such that microorganism growth on the surface of the device is possible. These include, but are not limited to, stents, catheters, cannulae, vascular grafts, artificial hearts, heart valves, venous valves, pacemakers and leads therefor, implantable defibrillators, implants, orthopedic pins and plates, artificial joints, prostheses, tracheal tubes, ventilator tubes, insulin pumps, wound closures, drains, shunts, connectors and those other medical devices typically used in an environment where antibacterial properties are desirable.

EXAMPLES

Example 1

A woven PET fabric (6"×6") was dipped in a 5% solution in THF of a styrene-ethylene-butylene-styrene triblock copolymer (SEBS) sulfonated to 65% mole percent, based on styrene, removed and allowed to dry on a sheet of PTFE. This dip coating process was repeated twice. (Higher solids concentrations can be utilized and require fewer dips overall.) The dried, coated fabric was placed into an aqueous solution of sodium bicarbonate ($NaHCO_3$) for about 1 hour to yield the sodium salt of the styrene sulfonate polymer, SEBS sodium sulfonate. The coated fabric was washed to remove excess sodium bicarbonate, dried and placed into an 10M aqueous solution of sodium sulfadiazine and allowed to equilibrate (fully hydrate). The fabric was then removed and placed into a bath of silver nitrate ($AgNO_3$). Metathesis of the silver and sodium afforded the insoluble silver sulfadiazine (SSD) entrapped into the copolymer. Crystalline silver sulfadiazine was visible at the surface and at high magnification could be seen protruding from the copolymer surface.

Example 2

A solution of silver sulfadiazine was prepared from silver nitrate and sodium sulfadiazine (Sigma Chemical) and blended with a sulfonated styrene-ethylene-butylene-styrene triblock copolymer (SSEBS) lacquer in THF as the solvent (5–10% solids sulfonated SEBS, 10% sodium sulfadiazine, w/w based on polymer). Fabric was coated by dipping into the lacquer-salt blend. The coated fabric was uniform and the silver sulfadiazine was uniformly distributed as determined by microscopy.

Example 3

SSEBS and Benzyltrimethylammoniumchloride

The sodium salt of SSEBS, supported on PET fabric, as prepared in example 1 above, was placed in an aqueous solution of benzyltrimethyl ammonium chloride. The composite was allowed to hydrate and equilibrate, yielding the benzyltrimethylammonium (BTMA) salt of SSEBS (SSEBS-BTMA). BTMA acts as a preservative for the dressing, in addition to providing disinfecting and antiviral properties.

Example 4

SSEBS and Benzocaine (Anesthetic)

Benzocaine (ethyl-p-aminobenzoate HCl) is added to a SSEBS lacquer as the free amine or as the HCl salt. Other amine-functional therapeutic agents may be bound to the acid form of the polymer in this fashion.

Example 5

SSEBS and RGD Peptide

RGD peptide was dissolved into phosphate buffered saline and the dressing was added. The dressing was allowed to equilibrate for one hour, removed, rinsed in DI water and dried. The presence of the peptide was confirmed by IR spectroscopy.

Example 6

SSEBS and Growth Factor (VEGF)

VEGF is incorporated using a method similar to that described above in example 5. The coated fabric is hydrated in an aqueous buffered solution containing the VEGF protein (with controlled temperature). SSEBS is an excellent substrate for binding and releasing the protein.

Example 7

SSEBS and Nonoxynol-9 (Antiviral/spermicide)

Nonoxynol-9 is added to a SSEBS lacquer. The structure of the therapeutic agent lends itself well to solubility in the SSEBS backbone, providing an excellent means for diffuision controlled release of this agent.

Example 8

Silver-filled Styrene Sulfonate Polymer

A SSEBS-coated fabric, prepared as in example 1, was placed into an aqueous solution of sodium bicarbonate, and soaked for about 24 hours. The fabric was placed in 1M aqueous solution of silver nitrate in a brown glass jar in a dark cabinet. The silver-containing fabric was then placed into a bath of hot aqueous sodium thiosulfate ($Na_2S_2O_7$). The color of the fabric began to change almost immediately. First, a white precipitate formed, then the fabric took on a yellowish color, then a gray, and finally a somewhat dull, yet uniform silver color. The fabric was removed and placed into a bath of sodium bicarbonate in order to neutralize the acid formed. When hydrated, the film was very supple and soothing to the touch.

The silver was evenly dispersed and not macro-particulate in nature. Its presence did not disrupt the surface of the copolymer. Analysis under SEM found no visible particulates. Elemental analysis showed a nearly 1:1:1 relationship between S:Ag:Na.

Example 9

A PET fabric is first sputter-coated with platinum and then coated with SSEBS. The silver-containing copolymer is prepared as in example 8. This dressing behaves as a silver ion iontophoretic pump between dissimilar metals Ag and Pt. Thus, galvanic corrosion of Ag leads to the formation of $Ag^+$ and an electron. The dressing retains the ability to absorb water and provide a soothing/cooling environment to the skin or wound.

What is claimed is:

1. A wound dressing for covering a wound, said wound dressing comprising at least one layer having al least one surface contactable with the wound and having disposed thereon a styrene sulfonate copolymer having a molecular weight of at least 20,000 and comprising:

residues derived from at least one olefin comonomer; and

20–80% by weight residues derived from styrene and comprising at least 15 mole percent styrene sulfonate structural units of formula I:

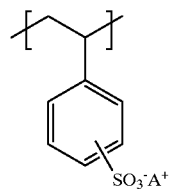

wherein $A^+$ is hydrogen ion, ammonium, an ion of an alkali metal, an ion of an oligodynamic metal or the cation of a therapeutic agent.

2. The wound dressing of claim 1, wherein said at least one layer is impregnated with said styrene sulfonate polymer.

3. The wound dressing of claim 1, wherein said at least one layer is coated with said styrene sulfonate polymer.

4. The wound dressing of claim 1, additionally comprising a second layer, said second layer comprising at least one of a solid film, a perforated film, a woven fabric, a nonwoven fabric, and a knit fabric.

5. The wound dressing of claim 1, additionally comprising a therapeutic agent.

6. The wound dressing of claim 5, wherein said therapeutic agent is at least one of an antibacterial agent, an anesthetic, a growth factor, a spermicide, an antiviral agent, an antifungal agent, an antiparisitic agent, an anti-inflammatory agent, an antihistamine, an analgesic agent, an antineoplastic agent, a hormone, a kerolytic agent, a tranquilizer, a vitamin, a base-pair nucleotide and a cytokine.

7. The wound dressing of claim 6, wherein said antibacterial agent is at least one of silver ion or silver metal.

8. The wound dressing of claim 1, wherein said olefin comonomer is at least one chosen from the group consisting of ethylene, propylene, butylene, isobutylene, butadiene and isoprene.

9. The wound dressing of claim 1, wherein said styrene sulfonate copolymer is a sulfonated styrene-ethylene-butylene-styrene triblock copolymer.

10. The wound dressing of claim 1, wherein said styrene sulfonate copolymer is a sulfonated reduced statistical styrene butadiene copolymer.

11. The wound dressing of claim 1, wherein said styrene sulfonate copolymer is a sulfonated statistical styrene ethylene copolymer.

12. The wound dressing of claim 1, wherein said styrene sulfonate copolymer is at least 35 mole percent sulfonated.

13. A wound dressing for covering a skin wound, said wound dressing comprising at least one layer having at least one surface contactable with the skin wound and having disposed thereon a polymer blend comprising a styrene sulfonate copolymer, said styrene sulfonate copolymer comprising residues derived from at least one olefin comonomer and structural units of formula I:

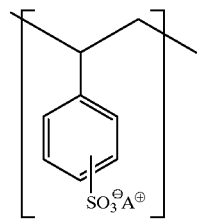

wherein $A^+$ is hydrogen, ammonium, an alkali metal, an oligodynamic metal or the cation of a therapeutic agent.

14. A process for the preparation of a hydrogel polymer comprising at least one of silver ion and silver metal, said process comprising:

combining the hydrogel polymer with aqueous silver ion; and optionally, at least partly reducing the silver ion to silver metal.

15. A process according to claim 14, wherein the silver metal has a particle size of 1000 nm or less.

16. A composition produced by the process of claim 14.

17. A coated implantable medical device comprising an implantable medical device having at least one surface, and a polymer disposed on a surface of said implantable device, said polymer comprising a composition according to claim 16.

18. A composition according to claim 16, comprising a silver salt of a styrene sulfonate copolymer.

19. A composition according to claim 16, comprising a styrene sulfonate copolymer and silver metal.

20. A composition according to claim 16, additionally comprising a non-silver metal.

21. A composition according to claim 16, additionally comprising a non-silver therapeutic agent.

22. The composition of claim 21, wherein said non-silver therapeutic agent is at least one of an antibacterial agent, an anesthetic, a growth factor, a spermicide, an antiviral agent, an antifungal agent, an antiparisitic agent, an anti-inflammatory agent, an antihistamine, an analgesic agent, an antineoplastic agent, a hormone, a kerolytic agent, a tranquilizer, a vitamin, a base-pair nucleotide and a cytokine.

23. The composition of claim 16, wherein said styrene sulfonate copolymer additionally comprises residues derived from at least one olefin comonomer.

24. The composition of claim 23, wherein said olefin comonomer is at least one chosen from the group consisting of ethylene, propylene, butylene, isobutylene, butadiene and isoprene.

25. The composition of claim 24, wherein said styrene sulfonate copolymer is a sulfonated styrene-ethylene-butylene-styrene triblock copolymer.

26. The composition of claim 24, wherein said styrene sulfonate copolymer is a sulfonated reduced statistical styrene butadiene copolymer.

27. The composition of claim 24, wherein said styrene sulfonate copolymer is a sulfonated statistical styrene ethylene copolymer.

28. The composition of claim 24, comprising a polymer blend of two or more of a sulfonated styrene-ethylene-butylene-styrene triblock copolymer, a sulfonated reduced statistical styrene butadiene copolymer, a sulfonated statis tical styrene ethylene copolymer and a sulfonated polystyrene.

29. The composition of claim 16, wherein said styrene sulfonate copolymer comprises from 20 to 80% styrene.

30. The composition of claim 16, wherein said styrene sulfonate copolymer has a molecular weight of at least 20,000.

31. The composition of claim 16, wherein said styrene sulfonate copolymer is at least 15 mole percent sulfonated.

32. The composition of claim 31, wherein said styrene sulfonate copolymer is at least 35 mole percent sulfonated.

33. A wound dressing according to claim 4, wherein said second layer comprises a woven fabric coated with platinum, a nonwoven fabric coated with platinum or a knit fabric coated with platinum.

* * * * *